United States Patent
Ross et al.

(10) Patent No.: US 7,718,046 B2
(45) Date of Patent: May 18, 2010

(54) MICELLAR GRADIENT FOCUSING

(75) Inventors: David J. Ross, Silver Spring, MD (US); Peter B. Howell, Gaithersburg, MD (US); Wyatt N. Vreeland, Washington, DC (US)

(73) Assignee: The United States of America, as represented by the Secretary of Commerce, the National Institute of Standards & Technology, Washington, DC (US)

( * ) Notice: Subject to any disclaimer, the term of this patent is extended or adjusted under 35 U.S.C. 154(b) by 1523 days.

(21) Appl. No.: 10/864,485

(22) Filed: Jun. 10, 2004

(65) Prior Publication Data

US 2004/0206626 A1    Oct. 21, 2004

(51) Int. Cl.
*B01D 57/02* (2006.01)
(52) U.S. Cl. ................. 204/450; 204/549; 204/551; 204/600; 204/645
(58) Field of Classification Search ......... 204/450–553, 204/600–650
See application file for complete search history.

(56) References Cited

U.S. PATENT DOCUMENTS 4,323,439 A * 4/1982 O'Farrell ............... 204/468
5,021,646 A * 6/1991 Weinberger et al. .... 250/227.11
6,331,235 B1 * 12/2001 Dolphin et al. ......... 204/451
2003/0019752 A1 * 1/2003 Ross et al. .............. 204/451

FOREIGN PATENT DOCUMENTS

WO    WO02/48673 * 6/2002

OTHER PUBLICATIONS

Zhu, Liang, Lee, Hian Kee, Lin, Bingcheng, Yeung, Edward, Spatial temperature gradient capillary electrophoresis for DNA mutation detection, 2001, Electrophoresis, 22, 3683-3687.*
L. Zhu et al; "Spatial temperature gradient capillary electrophoresis for DNA mutation detection"; Electrophoresis 2001, 22, 3683-3687.

* cited by examiner

*Primary Examiner*—Nam X Nguyen
*Assistant Examiner*—Bach T Dinh
(74) *Attorney, Agent, or Firm*—Stites & Harbison PLLC; Stephen J. Weyer; Ross F. Hunt, Jr.

(57) ABSTRACT

A method and device are provided for affinity gradient focusing for directing at least one analyte in a solution containing a pseudostationary phase and located in a channel such as a capillary or a microchannel. The method includes establishing a steady-state spatial gradient in a retention factor of the pseudostationary phase for the at least one analyte. The analyte is caused to be moved within the channel whereby the concentration of the at least one analyte changes at one or more positions along the gradient. The pseudostationary phase is charged and the analyte is either neutral or charged or alternatively, the pseudostationary phase is neutral and the analyte is charged. The device may include a fluid channel, a pseudostationary phase having a retention factor gradient, an electrical current source and a pump system for establishing the bulk flow in the solution in the channel.

11 Claims, 6 Drawing Sheets

FIGURES 3a-f

MICELLAR GRADIENT FOCUSING

FIELD OF THE INVENTION

The present invention relates to a method and device for separating and or concentrating one or more analytes in a solution, and in particular, to a method and device which focuses and separates analytes using affinity gradient focusing.

BACKGROUND OF THE INVENTION

Over the past decade a great deal of research has been focused on the development of micro-total-analytical systems. This technology is based on the concept of integration of a series of microfluidic channels for the movement, separation, reaction, and/or detection of various chemicals, e.g., proteins, DNA, chemical compounds, etc.

Prior methods for concentrating analytes include stacking and focusing. In the context of this disclosure, focusing refers to methods for manipulating the velocity of an analyte and thereby causing the analyte to move towards a point at which its velocity is zero and where the analyte will therefore accumulate and increase in concentration. In addition, the location of the zero velocity point is often dependent upon some characteristic of the analyte molecule being focused, so that different analyte molecules are focused at different points, and thereby separated.

In this context, focusing is to be distinguished from stacking, which is a related class of methods in which analytes are moved through a velocity gradient (which is often transient) and the analyte peaks become narrower and more concentrated, but there is no point of zero analyte velocity. In stacking methods, the maximum degree to which analyte concentration can be increased is theoretically limited to the ratio of the velocities on the fast and slow sides of the velocity gradient. In contrast, for focusing at a zero velocity point, there is no theoretical limit to the concentration factor.

Previously known focusing methods include isoelectric focusing (hereinafter "IEF"), electric field gradient focusing (hereinafter "EMF"), counteracting chromatographic electrophoresis, and temperature gradient focusing (hereinafter "TGF"). In general, all of these previously known methods work by creating a gradient in the electrophoretic velocity of the analyte. Therefore, they only work with analytes that have non-zero electrophoretic mobility. For example, in IEF, the analyte has zero electrophoretic mobility only at the zero velocity point.

Micellar electrokinetic chromatography and related methods (hereinafter "EKC") take advantage of an analyte's affinity for a pseudostationary phase to facilitate separations using capillary electrophoresis. Traditional EKC separations differ from traditional focusing techniques in that analyte molecules move along a separation channel at an essentially constant velocity, whereas in focusing techniques, analytes migrate through the channel to a point where they have a zero velocity. Separation in EKC is achieved because different analytes migrate with different velocities dependent on their affinity for the pseudostationary phase. Often EKC separations are implemented in conjunction with stacking procedures to preconcentrate analytes and facilitate lower detection limits.

In EKC (and in chromatography in general), the buffer is referred to as the mobile phase, and a second phase such as a micellar phase is referred to as the pseudostationary phase. The pseudostationary phase serves the same function—to provide selectivity—as a stationary phase in chromatography, but is not actually stationary, and can move with the buffer and/or with its own electrophoretic mobility.

SUMMARY OF THE INVENTION

The invention provides a method for the preconcentration and or separation of analytes in solution. In particular, it provides a focusing method for analytes that cannot be separated or focused based purely upon their electrophoretic mobilities (neutral species, or chiral species, for example). The separation can be used as a part of a chemical or biochemical analysis in a microfluidic chip or capillary system.

The new method, described here, combines the two concepts of focusing and EKC to achieve something that could not be done with either of them separately: the focusing of analytes based upon their affinity for a pseudostationary chromatographic phase. The new method combines the characteristics and utility of EKC with those of focusing wherein the pseudostationary phase provides a medium for analytes to move at differing velocities along the separation channel, and hence facilitate a focusing separation modality.

In one form of the invention, a method is provided for directing at least one analyte in a solution containing a pseudostationary phase. The method includes establishing a steady-state gradient in the retention factor of the pseudostationary phase for the at least one analyte. In one further embodiment the method further includes moving the at least one analyte in the solution, so that the concentration of the at least one analyte is caused to change at one or more positions along the gradient.

The present invention in another form thereof concerns a device for equilibrium gradient focusing which includes a separation channel and a solution containing a pseudostationary phase located in the separation channel. A first means produces a steady-state gradient in the retention factor of the pseudostationary phase for at least one analyte. In a further embodiment, the device includes a second means which provides movement of at least one analyte within the separation channel so that concentration of the at least one analyte is caused to increase at one or more positions along the separation channel.

In various alternate further embodiments, the first means provides for a temperature gradient along the length of the separation channel or creates a steady-state gradient in the composition of the solution. The temperature gradient can be produced using a heat sink or a heat source thermally coupled to the separation conduit. In an alternative form, the second means comprises a power supply for applying an electric field along the separator channel and means for applying a bulk flow of the solution through the separation channel, where the means may include a pump, or the means may include the same power supply which provides for moving the analyte, whereby the bulk flow is driven by electroosmosis. In yet another alternative form, the first means includes a fluid chamber containing a second solution to which is largely disconnected from the separation channel a semi-permeable structure connecting the fluid chamber to the separation channel, allowing passage of one or more components of the solution and the second solution.

In its implementation, the present method functions to focus or separate analytes using either a neutral or charged pseudostationary phase. For example, the pseudostationary phase may be charged micelles such as negatively charged micelles, although the same principles discussed apply for positively charged micelles. A voltage is applied so that the charged micelles move from the region of high retention to the region of low retention. The background buffer is made to flow in the opposite direction, from the region of low retention to the region of high retention. In the region of high retention, the analyte is predominantly located within the micelles and so the analyte moves with the micelles. In the region of low retention, the analyte is predominantly located outside the micelles, and so moves with the buffer, in the opposite direction. Somewhere between the regions of high and low retention, the net velocity of the analyte is zero, and the analyte is focused at that point.

An advantage of this method over all of the previous focusing techniques is that it can be used with neutral analytes, which, in their native state, have zero electrophoretic mobility. An additional advantage over other focusing techniques is that it provides for focusing based upon properties of the analyte molecules other than the electrophoretic mobility of the molecule.

An advantage of this method over the previous EKC techniques is that the present method is a focusing technique and as such has no theoretical upper limit to the concentration factor. An additional advantage over EKC stacking techniques is that the position of the focused analyte can be manipulated, e.g., held stationary or moved, as needed to maneuver the sample for detection or further analysis while maintaining the sample in a narrow focused plug.

An advantage of this method over prior art stacking or sweeping methods is that this method employs a steady-state gradient in the retention factor. This differs from stacking or sweeping methods in which a transient retention factor gradient is established by sequentially injecting two or more solutions with different compositions into a separation channel in order to form a composition (and therefore retention factor) gradient at the interface between two different solutions. These types of gradients used for stacking or sweeping change over time after they have been established either being dissipated by dispersion/diffusion and/or moving along the length of the separation channel. In contrast, the steady state gradients used by this method are established and maintained by the externally-controllable parameters of the method (the applied voltage, bulk flow rate, temperature, etc.), and as long as those parameters are kept constant, the gradient will persist. With this method, it is possible, however, to vary the gradient over time, in a controlled manner, by varying the externally-controllable parameters of the method.

Further features and advantages of the present invention will be set forth in, or apparent from, the detailed description of preferred embodiments thereof which follows.

BRIEF DESCRIPTION OF THE DRAWINGS

FIGS. 3a-f depict fluorescence microscopy images of focusing of rhodamine B where the images of FIGS. 3a-f were taken just before initiating the focusing, i.e., 0 seconds, and at 10, 20, 30, 40, and 50 seconds, respectively, after the voltage was turned on;

DETAILED DESCRIPTION OF THE PREFERRED EMBODIMENTS

The present method provides focusing, i.e., concentrations and/or separation, based upon affinity of an analyte for a pseudostationary phase such as a micellar phase. The method works by creating a steady-state gradient in the retention factor of the solute of interest to the pseudostationary phase (i.e., affinity of solute for the micelles) in a separation channel such as in capillary systems or in a microfluidic chip. The solute has an inherent electrophoretic mobility when free in solution. When interacting with the pseudostationary phase, the solute assumes the electrophoretic mobility of the pseudostationary phase. On one side of the gradient, the solutes strongly interact with the pseudostationary phase and have a net mobility dominated by that of the pseudostationary phase. On the other side of the gradient, the retention factor is low and the solute assumes its native electrophoretic mobility. If the pseudostationary phase is charged, a combination of electrokinetic and pressure-driven flow can be applied so that the pseudostationary phase and the mobile phase move in opposite directions. Conversely, focusing can be performed with a neutral pseudostationary phase if the analyte is charged and made to migrate in the opposite direction of the mobile phase. Under these conditions, the analyte can be made to focus at a point along the retention factor gradient. Different analytes with different affinities for the pseudostationary phase (or different electrophoretic mobilities) will focus at different points. The present method thereby provides a focusing equivalent of EKC.

Figure 1:
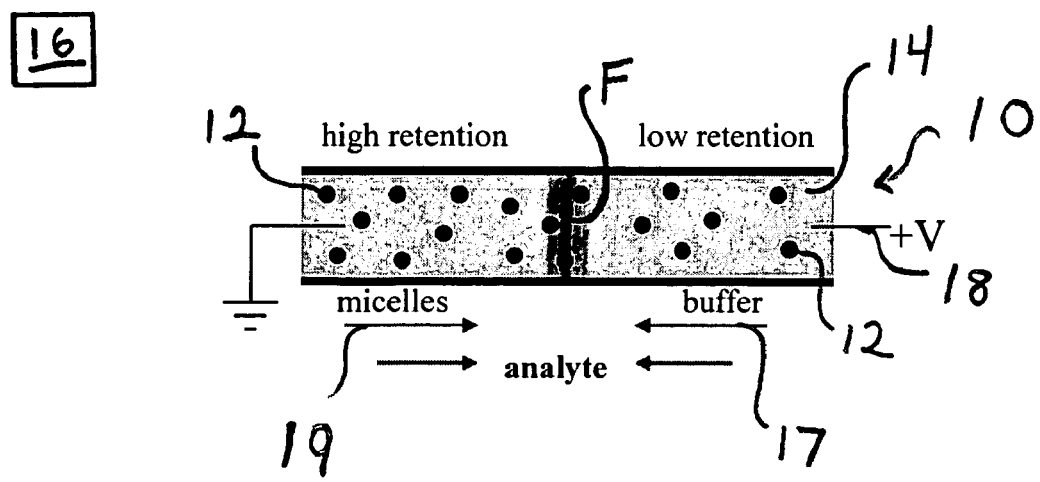
FIG. 1 is a schematic of micellar gradient focusing in a separation channel such as a microchannel or capillary.

Referring now to FIG. 1, on the left side of channel 10, the retention factor of an analyte in the micellar phase, or other pseudostationary phase as represented by micelles 12, is high, so that the analyte is predominantly found in the micelles 12. In the context of this patent, a separation channel refers to any microchannel, capillary, or other tube or separation column where the focusing and separation takes place. On the right side of channel 10, the retention factor is low, and the analyte is predominantly found in the mobile phase, i.e., buffer 14. The mobile phase is pumped via pump system 16, either electroosmotically, with pressure gradients, or by a combination of the two, so that the buffer 14 moves from the region of low retention factor to the region of high retention factor as indicated by arrow 17.

In the embodiment of FIG. 1, the micelles 12 are negatively charged, and a voltage is applied via power supply 18 to the channel 10 so that the micelles 12 electrophoretically migrate from the region of high retention factor to the region of low retention factor as indicated by arrow 19. In the region of high retention factor, the analyte moves primarily with the micelles 12. In the region of low retention factor, the analyte moves primarily with the mobile phase, i.e., buffer 14. The result is that the analyte moves toward the center from both ends of the channel and is focused at some point F along the retention factor gradient at which the net velocity of the analyte is zero. Although the embodiment of FIG. 1 has the micelles being negatively charged, one skilled in the art will readily appreciate that the same focusing technique can easily be modified for positively charged micelles.

Although the present micellar gradient focusing bears similarities in its implementation to temperature gradient focusing, micellar gradient focusing focuses analytes via a different mechanism and is functionally unique from temperature gradient focusing. Further, it is important to note that whereas temperature gradient focusing requires a buffer whose ionic strength is a function of temperature, micellar gradient focusing can be accomplished in any buffer capable of supporting a pseudostationary phase.

Micellar gradient focusing requires the production of a spatial gradient in the analyte velocity. For the motion of an analyte in a system such as that illustrated in FIG. 1, the total analyte velocity is given by:

$$u_T = (u_B + u_{EP}) \cdot [1/(1+k)] + u_{MC} \cdot [k/(1+k)],$$

where $u_B$ is the mobile phase velocity, $u_{EP}$ is the electrophoretic velocity of the analyte through the mobile phase (equal to zero for neutral analytes), $u_{MC}$ is the (total) velocity of the micelles, and k is the retention factor (a factor indicating the relative amount of time the analyte spends in the pseudostationary phase). This description describes methods to produce the required velocity gradient by producing a gradient in the retention factor k.

The retention factor is equal to $k=K\beta$, where K is the distribution coefficient which quantifies the affinity of the analyte for the pseudostationary phase, and $\beta$ is the phase ratio defined as the ratio of the volume of pseudostationary phase to the volume of mobile phase. The production of a retention factor gradient can then be accomplished either through a gradient in the distribution coefficient or through a gradient in the phase ratio or a combination of the two. There are several different ways that this can be accomplished, some of which are listed below.

A solution of surfactant will form micelles if and only if the concentration of surfactant is greater than the critical micelle concentration (hereinafter "CMC"). For surfactant concentration greater than the CMC, the volume of micellar pseudostationary phase is proportional to the difference between the concentration and the CMC. For most surfactants, the CMC is a function of temperature. Therefore, a gradient in the phase ratio can then be obtained by applying a temperature gradient at a fixed surfactant concentration.

Figure 2:
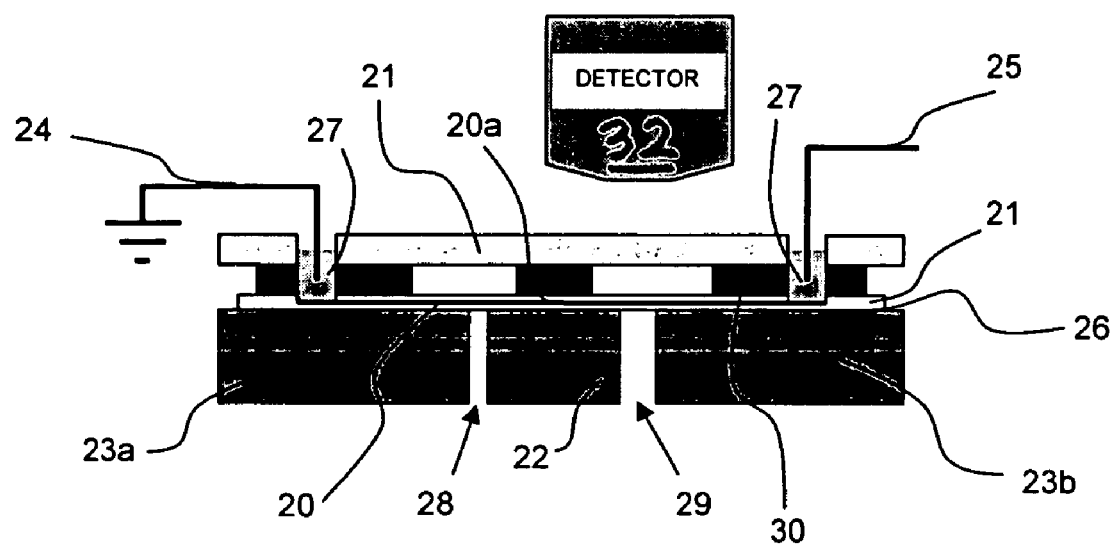
FIG. 2 is a schematic drawing of a fluidic device according to one embodiment of the present invention.

Implementation of this embodiment is described with reference to a microfluidic chip exemplar having a microchannel 20 as shown in FIG. 2 which is one possible apparatus for controlling the temperature of different parts of the microchannel. The method of creating a temperature gradient is the same as described in U.S. patent application Ser. No. 10/197,331, herein incorporated by reference. However, the apparatus of U.S. patent application Ser. No. 10/197,331 provides for just one of many different ways to manipulate the temperature in a microchannel which are known to one of ordinary skill in the art.

In the embodiment, the buffer is 5 mM carbonate buffer, pH 9.4 in approximately 5% by weight ethanol, 95% water, with a 5 mM concentration of sodium dodecyl sulfate (SDS). For an analyte, the neutral fluorescent dye rhodamine B is added to the solution at a concentration of about 2.5 µM. For this type of SDS solution the CMC is an increasing function of temperature, so that the phase ratio is a decreasing function of temperature.

A microchannel 20 with dimensions 30 µm deep, 50 µm wide, and 2 cm long is used for the separation. The microchannel and fluid reservoirs 27 are initially filled with the uniform sample solution. The temperatures of the cold and hot portions of the apparatus are set to 10° C. and 80° C. using heat sinks such as cooling copper blocks 23a, 23b covering much of the ends of the microchannel 20, and one hot zone provided by a heat source such as heated copper block 22. Thermal contact between the poly(carbonate) and the copper blocks is insured using a thermally conductive adhesive 26. The copper blocks 22, 23a, 23b are arranged so that there was a 1 mm gap 28 between the heated copper block 22 and the cooling copper block 23a and a 2 mm gap 29 between heated copper block 22 and the cooling copper block 23b.

Microchannel 20 also includes electrodes 25, 24, input wells, i.e., buffer reservoirs 27 for the mobile phase buffer, and a narrow hot zone 20a near the middle of the microchannel 20. The heated copper block 22 is heated using a small high-power resistor embedded into the copper and its temperature is regulated using a PID temperature controller (Omega Engineering Inc., Stamford, Conn.). To regulate the temperature of the cold zones, ¼ inch diameter holes are drilled through the cooling copper blocks 23a, 23b and cold water from a thermostatted bath (Neslab, Portsmouth, N.H.) is passed through them. The amount of solution in the input wells at each end of the channel 20 is adjusted to produce pressure-driven flow so that when a voltage is applied, the micelles would move from cold to hot above the 1 mm gap while the mobile phase would move from hot to cold above the gap.

Figure 3:
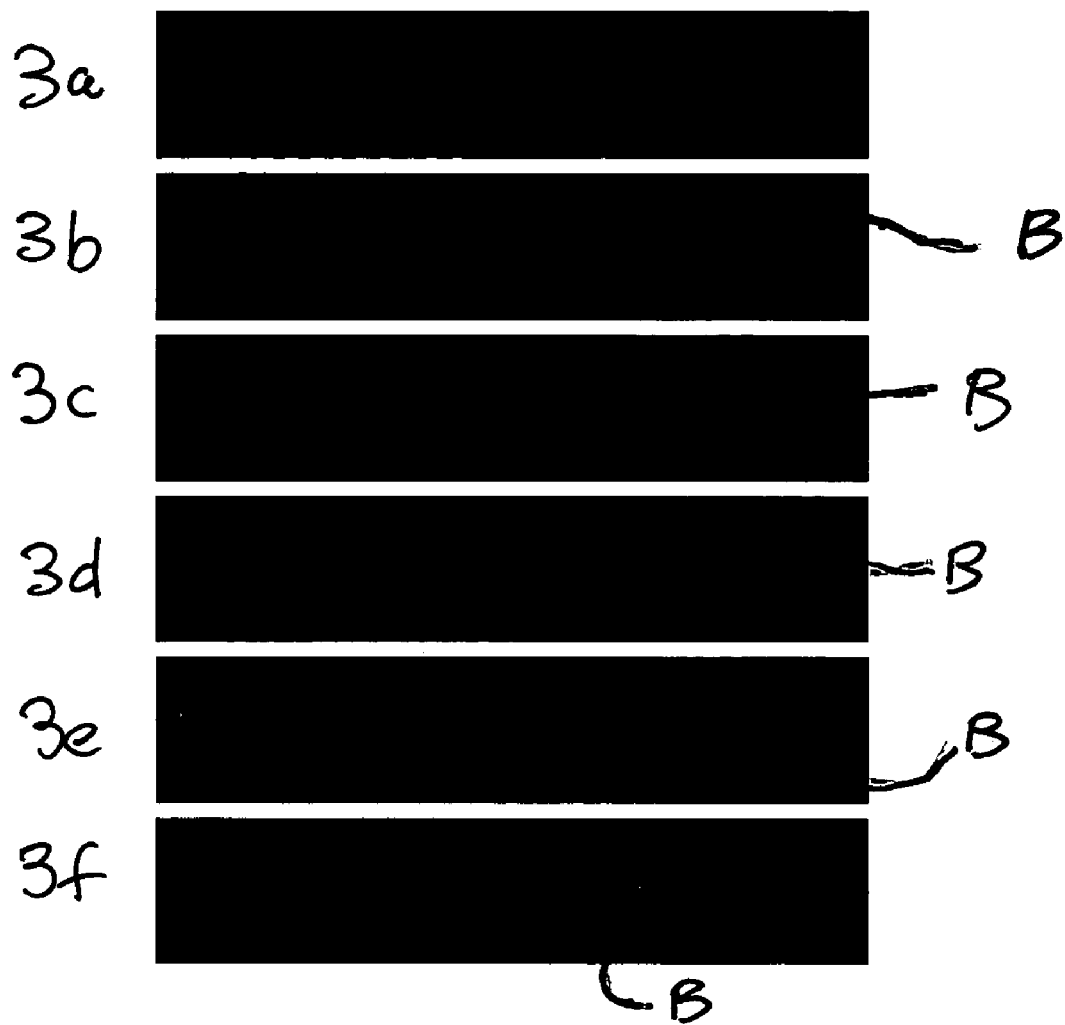

A voltage of +125 V is applied, and the distribution of rhodamine B dye in the channel is monitored using a fluorescence microscope and CCD camera 32. A series of the resulting images taken at 10 second intervals from 0 to 50 seconds as is shown in FIGS. 3a-3f, respectively with the rhodamine B identified as B. After 50 seconds, a bright band of focused rhodamine was clearly visible near the hot end (the right side in the figure) of the temperature gradient (FIG. 3f).

The same apparatus as described above can be used to produce the temperature gradient in a capillary. The solution used is similar to that used for the device in a microchannel, and consists of 20 mM SDS, and 5 mM carbonate buffer in 25% ethanol, 75% water. An initial concentration of rhodamine B of 0.2 µM is used.

Figure 4:
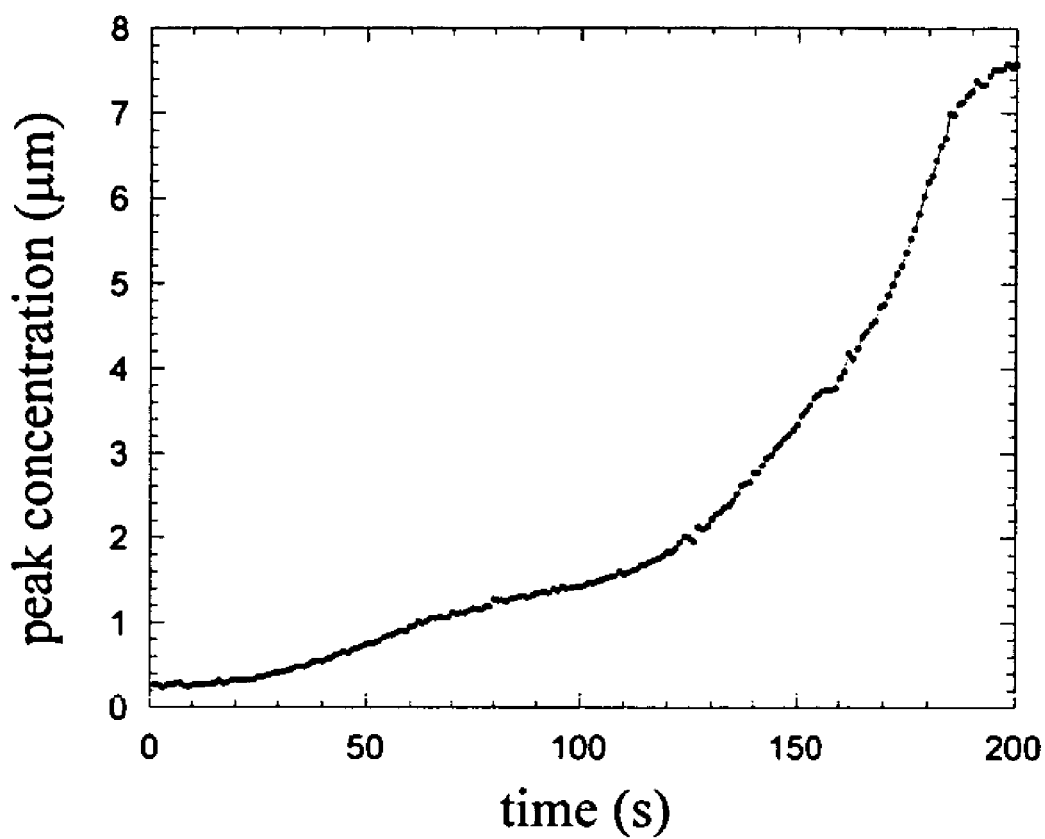
FIG. 4 is a plot of peak concentration vs. time for focusing of rhodamine B in a capillary.

FIG. 4 shows a plot of the focused peak concentration, inferred from the measured fluorescence intensities, as a function of time. After the voltage is switched on around 5 seconds, the peak concentration increased with time, reaching a value greater than 7 µM in about 3 minutes. About a 35-fold increase in concentration is achieved in three minutes.

Figure 5:
FIG. 5 depicts micellar gradient focusing and separation of two neutral fluorescent dyes, rhodamine B (left) and rhodamine 110 (right)

Referring now to FIG. 5, in a further embodiment, the present method can be used for focusing and separating more than one species in a capillary. Building on the embodiment of FIGS. 2 and 3 from above for focusing rhodamine B, after the rhodamine B is focused for several minutes, identified as B, a solution of approximately 3 µM rhodamine 110 is introduced at the entrance to the capillary. After a few minutes of additional focusing, the rhodamine 110 was clearly visible as an additional focused peak as shown in FIG. 5 identified as 110. Note that in normal operation, a separation would be accomplished by injecting mixed sample into the separation channel rather than by sequential injection of different samples as was done for this demonstration.

In most cases the distribution coefficient is temperature-dependent, so that a retention factor gradient could be made by applying a temperature gradient, even if the CMC and the phase ratio were temperature-independent. In the above example, there is probably a combination of these two temperature-dependent effects that contribute to the focusing.

There have also been pseudostationary phases specifically developed to provide a temperature-dependent affinity for various analytes. These are used in "temperature-programming" EKC, where the temperature of the separation is changed over time to achieve improved separations. Use of these types of pseudostationary phases for focusing with a temperature gradient according to the methods described herein would be relatively straight forward and readily implemented by one skilled in the art. Examples include the use of a thermoresponsive polymer poly(N-isopropyl-acrylamide), which can be used to make pseudostationary phases that can be switched on and off at a transition temperature.

Both the distribution coefficient and phase ratio can be dependant upon the composition of the solution used, and so a retention factor gradient can be produced using a gradient in the solution composition.

Figure 6:
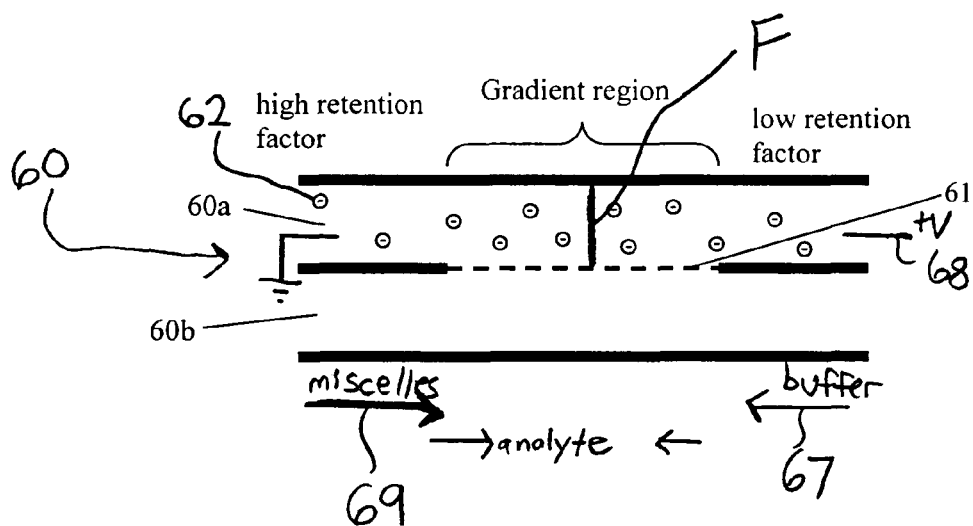
FIG. 6 is a schematic of micellar gradient focusing in a separation conduit according to another embodiment of the present invention.

Referring now to FIG. 6, in another embodiment, of a separation conduit, such as a microchannel or capillary for use in gradient focusing, where like elements to the embodiment of FIG. 1 are identified as reference numbers increased by 50, microchannel 60 is divided into two adjacent conduits, separation channel 60a and control channel 60b. The two channels over a certain portion of their length, the gradient region, are connected by a selectively-permeable membrane or other selectively permeable structure 61. The analyte and the pseudostationary phase are contained in the separation channel 60a. As in the embodiment of FIG. 1, the solution in the separation channel 60a is caused to flow from the region of low retention factor to the region of high retention factor. The control channel 60b and the membrane 61 are used to form a gradient in one or more components of the buffer in the separation channel 60a and to thereby form the retention factor gradient. The control channel 60b contains a solution of a composition differing from that in the separation channel 60a. The difference between the two solutions will most often be in the concentration of one or more of the solution components. The membrane is chosen to be permeable to one or more of the components that are present in differing concentrations in the two solutions. The passage of the solution components through the membrane will cause the composition of the solution in the separation channel to change. Because the solution in the separation channel 60a is flowing from the region of low retention factor to the region of high retention factor, this change will be greater at the high retention factor end of the gradient region than at the low retention factor end. Thus, a steady-state gradient in the composition of the solution in the separation channel 60a will be established.

The composition gradient can be, for example, a gradient in the surfactant concentration in a micellar system, or a gradient in the concentration of an organic modifier, or a gradient in the concentration of a salt dissolved in the solution. Because the retention factor is a function of the composition of the solution used, this will result in a steady-state gradient of the retention factor in the separation channel. This retention factor gradient can then be used for focusing as in the previously described embodiments.

Note that the geometrical arrangement of the separation channel 60a and the control channel 60b need not be side-by-side as drawn in FIG. 6. They could also be arranged coaxially, annularly, or in any other arrangement that accomplished the desired solution composition gradient. In addition, the relative sizes of the two channels need not be equal as is shown in FIG. 6. The control channel could in fact be replaced with a much larger container of solution. For examples of devices using similar semi-permeable structures to separate two channels see Z. Huang and C. F. Ivory, Analytical Chemistry 71, 1628 (1999); Z. Huang and C. F. Ivory, Abstracts of Papers of the American Chemical Society 219, 208-BIOT (2000); and S. Song, A. K. Singh, T. J. Shepodd, and B. J. Kirby, Analytical Chemistry 2004, vol. 76, p. 2367, all herein incorporated by reference.

As previously noted, materials and strategies that have been developed for EKC methods could be modified and applied to the present method as would be now readily apparent to one of ordinary skill in the art. For example, it is common in EKC to vary the solution composition (e.g., salt concentration, fraction of alcohol used, surfactant concentration, etc.) as a function of time to produce a time variation of the retention factor. These strategies—referred to as "solvent programming"—could be combined with a spatial gradient of the solution composition to produce a spatial gradient of the retention factor that could be used for focusing.

A neutral micellar or other pseudostationary phase would always move with the bulk buffer. In this case, Equation (1) would become:

$$u_T = u_B + u_{EP}[1/(1+k)].$$

Because the electrophoretic mobility of the analyte changes when it moves from the mobile phase to the pseudostationary phase, a gradient in the retention factor will still produce a gradient in velocity (if $u_{EP} \neq 0$), and so a neutral micellar or other pseudostationary phase can be used for focusing. If the analyte is neutral, however, the pseudostationary phase must be charged.

The present micellar gradient focusing can also be implemented through the superposition of multiple separation modalities to yield highly selective chiral separations. Traditionally, microchannel-based separations of chiral analytes are conducted by adding a chiral selector to the medium in which the separation is performed. Commonly these chiral selectors have a chiral handedness associated with their structure and thereby interact more strongly with either the D or L enantiomer of a racemic analyte mixture. This interaction either will lead to a retardation of the electrophoretic velocity of one enantiomer over the other and or differentially effect the partitioning into the pseudostationary phase, and thereby provide their separation.

Implementation of chiral selectors in the present method can be done by adding the desired chiral selector (in addition to the pseudostationary phase) to the buffer medium. Thus, the addition of the chiral selector would effect the velocities (and therefore the focusing points) of the two enantiomers differently in one or both of two ways: the chiral selector could either differentially modify the electrophoretic mobilities of the two enantiomers and/or it could differentially effect their partitioning into the pseudostationary phase. Thus micellar gradient focusing, where a spatial gradient in pseudostationary phase affinity for the analyte exists, allows for focusing of enantiomers at differing spatial points in the channel when combined with a chiral selector. Note that chiral separations could also be accomplished within this new method by using a chiral pseudostationary phase, such as micelles formed with chiral surfactants, either with or without an additional chiral selector additive.

It will now be apparent to one skilled in the art that the present method combines focusing with EKC and thereby incorporates the advantages of both. Advantages inherent to focusing include the high degree of analyte concentration that can be achieved which translates to lower concentration limits of detection, simultaneous separation and concentration of one or more analytes of interest, and the ability to manipulate the sample peak while maintaining focusing.

The combination of focusing with micellar chromatography adds the ability to focus and separate analytes that cannot be focused or separated with any other prior focusing technique. In particular, neutral species now can be focused, and different analytes with identical electrophoretic mobilities, such as stereo-isomers, can be separated.

Further, the pseudostationary-phase-based focusing of the present invention also allows for the tuning of the property of the analyte molecules that is the basis for the focusing and separation. For example, different pseudostationary phases can be used to separate analytes based upon their hydrophobicity, chirality, or specific affinity for a ligand. Any of the pseudostationary phases that have been developed for EKC can potentially be used in a focusing mode with the present novel method.

In addition, the present micellar gradient focusing technique, which separates molecules on the basis of properties other than electrophoretic mobility, can be used in conjunction with one of the previously developed focusing techniques or in combination with a different variation or embodiment of this present micellar gradient focusing technique to implement a 2D separation scheme in which both separation dimensions result from focusing techniques.

Since the retention factor gradient can be imposed using a temperature gradient, the present method potentially shares the advantage of the simplicity of implementation of temperature gradient focusing.

Although the invention has been described above in relation to preferred embodiments thereof, it will be understood by those skilled in the art that variations and modifications can be effected in these preferred embodiments without departing from the scope and spirit of the invention.

The invention claimed is:

1. A method for directing at least one analyte in a solution containing a pseudostationary phase, the pseudostationary phase having a retention factor for said at least one analyte, said method comprising the steps of:
    establishing a steady-state spatial gradient in the retention factor in the pseudostationary phase for the at least one analyte; and
    moving the at least one analyte in the solution, so that the concentration of the at least one analyte is caused to change at one or more positions along said gradient, wherein said moving the at least one analyte is accomplished using a combination of an applied electric field and an applied bulk solution flow, wherein:
    the pseudostationary phase is an ionic pseudostationary phase;
    the analyte is either neutral or charged;
    the applied electric field has a significant component substantially aligned with said gradient and in a direction such that the resulting electrophoretic motion of the ionic pseudostationary phase is substantially aligned in a direction from a region of high retention factor to a region of low retention factor; and
    the applied bulk solution flow has a significant component substantially aligned in a direction opposite the direction of the electrophoretic motion of the ionic pseudostationary phase.

2. The method of claim 1, wherein said step of establishing a steady-state spatial gradient in the retention factor comprises producing a temperature gradient in the solution.

3. The method of claim 1, wherein said step of establishing a steady-state spatial gradient in the retention factor comprises producing a gradient in the composition of the solution.

4. The method of claim 1, further comprising adding a chiral selector to the solution.

5. The method of claim 1, wherein the pseudostationary phase is selected from the group comprising micelles, microemulsions, lyposomes, and dendrimers.

6. A method for directing at least one analyte in a solution containing a pseudostationary phase, the pseudostationary phase having a retention factor for said at least one analyte, said method comprising the steps of:
    establishing a steady-state spatial gradient in the retention factor in the pseudostationary phase for the at least one analyte by producing a gradient in the composition of the solution; and
    moving the at least one analyte in the solution, so that the concentration of the at least one analyte is caused to change at one or more positions along said gradient, moving the at least one analyte is accomplished using a combination of an applied electric field and an applied bulk solution flow, wherein:
    the pseudostationary phase is a neutral pseudostationary phase;
    the analyte is charged;
    the applied electric field has a significant component substantially aligned with said gradient and in a direction such that the resulting electrophoretic motion of the at least one ionic analyte is substantially aligned in a direction from a region of low retention factor to a region of high retention factor; and
    the applied bulk solution flow has a significant component substantially aligned in a direction opposite the direction of the electrophoretic motion of the at least one ionic analyte.

7. A method for directing at least one analyte in a solution containing a pseudostationary phase, the pseudostationary phase having a retention factor for said at least one analyte, said method comprising the steps of:
    establishing a steady-state spatial gradient in the retention factor in the pseudostationary phase for the at least one analyte;
    applying an electric field having a significant component substantially aligned with said gradient and in a direction such that the resulting electrophoretic motion of the ionic pseudostationary phase is substantially aligned in a direction from a region of high retention factor to a region of low retention factor; and
    applying bulk solution flow having a significant component substantially aligned in a direction opposite the direction of the electrophoretic motion of the ionic pseudostationary phase; wherein:
    the pseudostationary phase is an ionic pseudostationary phase; and
    the analyte is either neutral or charged.

8. The method of claim 7, wherein said step of establishing a steady-state spatial gradient in the retention factor comprises producing a temperature gradient in the solution.

9. The method of claim 7, wherein said step of establishing a steady-state spatial gradient in the retention factor comprises producing a gradient in the composition of the solution.

10. The method of claim 7, further comprising adding a chiral selector to the solution.

11. The method of claim 7, wherein the pseudostationary phase is selected from the group comprising micelles, microemulsions, lyposomes, and dendrimers.

* * * * *